(12) United States Patent
Nakagawa et al.

(10) Patent No.: US 10,085,705 B2
(45) Date of Patent: Oct. 2, 2018

(54) MEDICAL OBSERVATION SYSTEM

(71) Applicant: OLYMPUS CORPORATION, Tokyo (JP)

(72) Inventors: Sanae Nakagawa, Hachioji (JP); Junichi Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 15 days.

(21) Appl. No.: 15/462,189

(22) Filed: Mar. 17, 2017

(65) Prior Publication Data
US 2017/0188986 A1 Jul. 6, 2017

Related U.S. Application Data

(63) Continuation of application No. PCT/JP2015/058040, filed on Mar. 18, 2015.

(30) Foreign Application Priority Data

Sep. 19, 2014 (JP) .................................. 2014-191727

(51) Int. Cl.
*G06K 9/00* (2006.01)
*A61B 6/00* (2006.01)
(Continued)

(52) U.S. Cl.
CPC ............ *A61B 6/52* (2013.01); *A61B 1/00009* (2013.01); *A61B 6/03* (2013.01); *A61B 6/12* (2013.01);
(Continued)

(58) Field of Classification Search
CPC ................. A61B 5/00; A61B 6/00; G06T 7/00
(Continued)

(56) References Cited

U.S. PATENT DOCUMENTS 6,332,089 B1 * 12/2001 Acker .................. A61B 5/0422
128/899
7,912,262 B2 * 3/2011 Timmer ............... A61B 6/4441
128/922
(Continued)

FOREIGN PATENT DOCUMENTS

EP          2700351 A1    2/2014
JP       2012-005636 A    1/2012
(Continued)

OTHER PUBLICATIONS

International Search Report dated Jun. 16, 2015 issued in PCT/JP2015/058040.

*Primary Examiner* — Abolfazl Tabatabai
(74) *Attorney, Agent, or Firm* — Scully, Scott, Murphy & Presser, P.C.

(57) ABSTRACT

A medical observation system includes: a position information storage portion configured to perform processing for storing first position information indicating an initial position of an object for executing treatment in a three-dimensional image generated using a plurality of tomographic images of a subject; a movement detection portion configured to detect movement of the object; a position information acquisition portion configured to acquire second position information indicating a present position of the object in the three-dimensional image when the movement of the object is detected; and a display image generation portion configured to update a position of the object in the three-dimensional image from the first position information to the second position information in a case that the second position information is acquired, and generate an image superimposed on the three-dimensional image or on a pseudo fluoroscopic image generated based on the plurality of tomographic images.

12 Claims, 8 Drawing Sheets

(51) Int. Cl.
    *A61B 1/00*           (2006.01)
    *A61B 6/12*           (2006.01)
    *A61B 6/03*           (2006.01)
    *G06T 7/73*           (2017.01)
    *G06T 7/246*          (2017.01)
    *G06T 19/20*          (2011.01)

(52) U.S. Cl.
    CPC ............ *A61B 6/4441* (2013.01); *G06T 7/251* (2017.01); *G06T 7/75* (2017.01); *G06T 19/20* (2013.01); *G06T 2207/10028* (2013.01); *G06T 2207/10064* (2013.01); *G06T 2207/10068* (2013.01); *G06T 2207/10081* (2013.01); *G06T 2207/20221* (2013.01); *G06T 2207/30244* (2013.01); *G06T 2219/2004* (2013.01)

(58) Field of Classification Search
    USPC ........................................ 382/107; 378/4, 21
    See application file for complete search history.

(56) References Cited

U.S. PATENT DOCUMENTS

2014/0016851 A1    1/2014    Nakano
2014/0088357 A1    3/2014    Ikuma et al.

FOREIGN PATENT DOCUMENTS

| JP | 2013-527782 A | 7/2013 |
| --- | --- | --- |
| JP | 2013-212364 A | 10/2013 |
| JP | 5378628 B1 | 12/2013 |
| WO | WO 2013/132880 A1 | 9/2013 |
| WO | WO 2013/133288 A1 | 9/2013 |

\* cited by examiner

| TIME STAMP | COORDINATE VALUE IN REAL SPACE (DISTAL END POSITION DATA) | | | COORDINATE VALUE IN THREE-DIMENSIONAL DATA (DISTAL END POSITION DATA) | | |
|---|---|---|---|---|---|---|
| | X | Y | Z | X | Y | Z |
| TSP1 | A1 | B1 | C1 | D1 | E1 | F1 |
| TSP2 | A2 | B2 | C2 | D2 | E2 | F2 |
| TSP3 | A3 | B3 | C3 | D3 | E3 | F3 |
| TSP4 | A4 | B4 | C4 | D4 | E4 | F1 |
| TSP5 | A5 | B5 | C5 | D5 | E5 | F5 |
| ⋮ | ⋮ | ⋮ | ⋮ | ⋮ | ⋮ | ⋮ |
| TSPn | An | Bn | Cn | Dn | En | Fn |

| TIME STAMP | COORDINATE VALUE IN THREE-DIMENSIONAL DATA (STONE POSITION DATA) | | |
|---|---|---|---|
| | X | Y | Z |
| TSQ1 | G1 | H1 | I1 |
| TSQ2 | G2 | H2 | I2 |
| TSQ3 | G3 | H3 | I3 |
| TSQ4 | G4 | H4 | I4 |
| TSQ5 | G5 | H5 | I5 |
| ⋮ | ⋮ | ⋮ | ⋮ |
| TSQm | Gm | Hm | Im |

MEDICAL OBSERVATION SYSTEM

CROSS REFERENCE TO RELATED APPLICATION

This application is a continuation application of PCT/JP2015/058040 filed on Mar. 18, 2015 and claims benefit of Japanese Application No. 2014-191727 filed in Japan on Sep. 19, 2014, the entire contents of which are incorporated herein by this reference.

BACKGROUND OF THE INVENTION

1. Field of the Invention

The present invention relates to a medical observation system, and particularly relates to a medical observation system used to specify a position of a predetermined object existing inside a living body.

2. Description of the Related Art

As a treatment method for removing a stone inside a kidney, for example, treatment methods such as ESWL (extracorporeal shock wave lithotrity), TUL (transurethral ureterolithotomy) and f-TUL (flexible transurethral ureterolithotomy) are conventionally known.

In addition, for example, Japanese Patent Application Laid-Open Publication No. 2013-527782 discloses, as a treatment method for accelerating removal of a stone inside the kidney, a method of specifying a position of the stone using a known imaging modality such as fluoroscopy and applying extrusion ultrasound having a pressure amplitude of a predetermined range to the stone.

SUMMARY OF THE INVENTION

A medical observation system of one aspect of the present invention includes: a position information storage portion configured to perform processing for storing first position information which is information indicating an initial position of an object for executing treatment in a three-dimensional image generated based on a plurality of tomographic images of a subject; a movement detection portion configured to detect movement of the object for executing the treatment; a position information acquisition portion configured to perform processing for acquiring second position information which is information indicating a present position of the object for executing the treatment in the three-dimensional image when the movement of the object for executing the treatment is detected by the movement detection portion; and a display image generation portion configured to update a position of the object for executing the treatment in the three-dimensional image from the first position information to the second position information in a case that the second position information is acquired by the position information acquisition portion, and generate an image superimposed on the three-dimensional image or on a pseudo fluoroscopic image generated based on the plurality of tomographic images.

DETAILED DESCRIPTION OF THE PREFERRED EMBODIMENT

Hereinafter, an embodiment of the present invention will be described with reference to the drawings.

Figure 1:
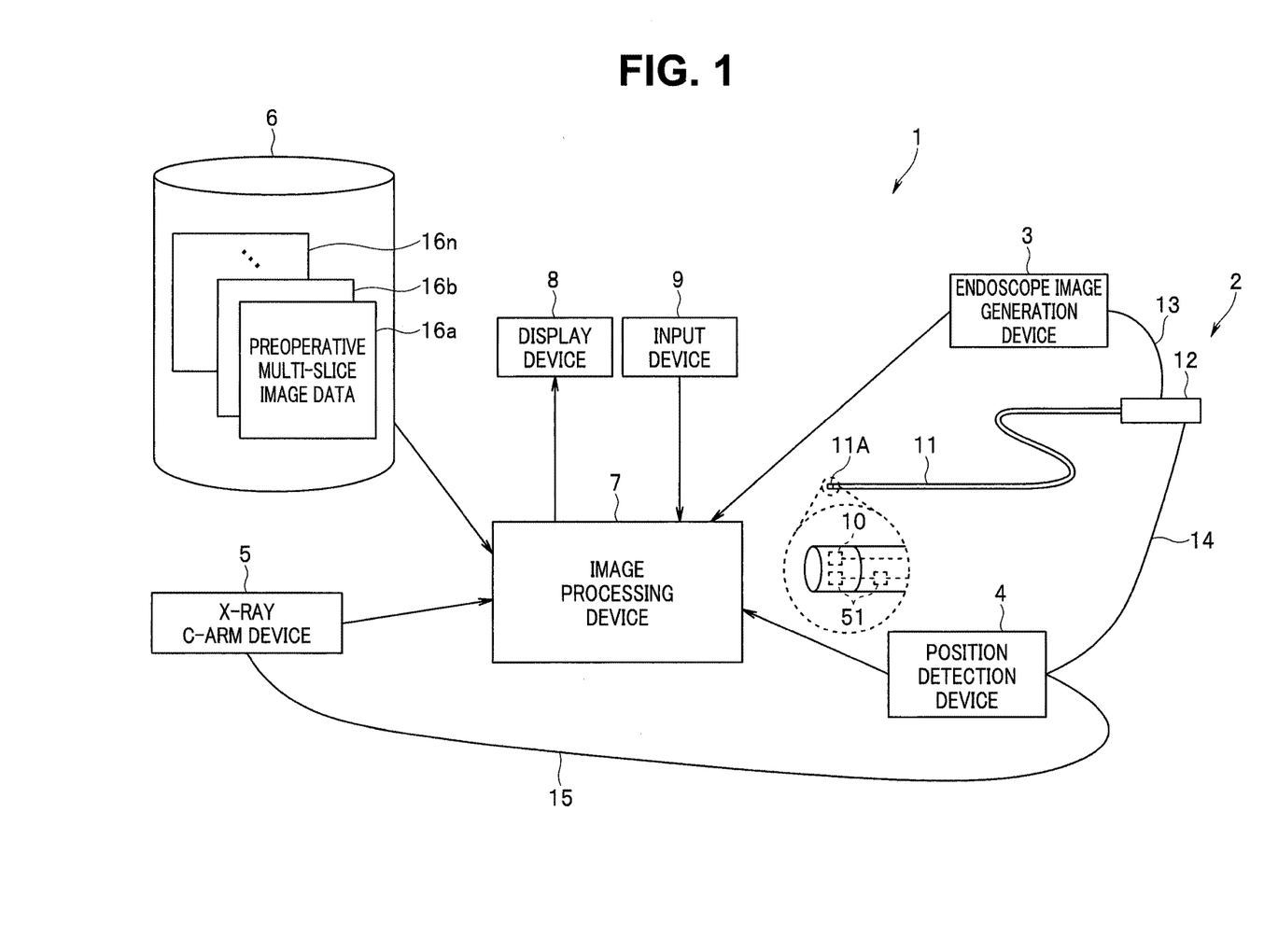
FIG. 1 is a diagram illustrating a configuration of a main portion of a medical observation system relating to an embodiment.

FIG. 1 to FIG. 12 relate to the embodiment of the present invention. FIG. 1 is a diagram illustrating a configuration of a main portion of a medical observation system relating to the embodiment.

As illustrated in FIG. 1, a medical observation system 1 is configured including an endoscope 2, an endoscope image generation device 3, a position detection device 4, an X-ray C-arm device 5, a server 6, an image processing device 7, a display device 8, and an input device 9.

The endoscope 2 is configured including an elongated insertion portion 11 insertable into a subject and formed with flexibility, an operation portion 12 connected to a proximal end portion of the insertion portion 11, and a cable 13 extended from a side face of the operation portion 12.

The endoscope 2 is configured to be connected through the cable 13 to the endoscope image generation device 3, and be connected through a cable 14 to the position detection device 4.

On a distal end portion 11A of the insertion portion 11, an image pickup portion 10 for picking up an image of an object inside the subject is provided.

The image pickup portion 10 is, for example, configured to pick up the image of the object by an image pickup device such as a CCD, and generate image pickup signals according to the object, the image of which is picked up. Then, the image pickup signals generated in the image pickup portion 10 are outputted through the operation portion 12 and the cable 13 to the endoscope image generation device 3.

At a part from the distal end portion 11A to a proximal end portion of the insertion portion 11, a plurality of magnetic sensors 51 that detect a magnetic field originated from the position detection device 4 and generate electric signals according to the detected magnetic field are disposed at every predetermined interval. Then, the electric signals generated in the plurality of magnetic sensors 51 are outputted through the operation portion 12 the cable 14 to the position detection device 4.

The endoscope image generation device 3 is configured to be connected to the endoscope 2 through the cable 13. In addition, the endoscope image generation device 3 is configured to generate endoscope image data by executing a predetermined image processing to the image pickup signals outputted from the endoscope 2 through the cable 13, and output the generated endoscope image data to the image processing device 7.

The position detection device 4 is configured to be connected to the endoscope 2 through the cable 14. In addition, the position detection device 4 is configured to extract the electric signals generated in the magnetic sensor 51 positioned on a most distal end side of the insertion portion 11 from the electric signals inputted through the cable 14, perform an arithmetic operation for detecting a position in real space and a direction of the distal end portion 11A of the insertion portion 11 based on the extracted electric signals at every predetermined time interval, generate distal end position data and distal end direction data indicating arithmetic results obtained by the arithmetic operation, and successively output the generated distal end position data and distal end direction data to the image processing device 7.

The position detection device 4 is configured to perform an arithmetic operation for detecting an insertion shape of the insertion portion 11 based on the electric signals inputted through the cable 14, generate insertion shape data indicating the arithmetic result obtained by the arithmetic operation, and output the generated insertion shape data to the image processing device 7.

The position detection device 4 is configured to perform an arithmetic operation for detecting a position of an X-ray C-arm (described later) in the X-ray C-arm device 5 or the like based on the electric signals inputted through a cable 15, generate X-ray image pickup position data indicating the arithmetic result obtained by the arithmetic operation, and output the generated X-ray image pickup position data to the image processing device 7.

The X-ray C-arm device 5 is configured including an X-ray generation portion configured to generate X-rays to be transmitted through the subject, and the X-ray C-arm provided with an X-ray detection portion for detecting the X-rays originated from the X-ray generation portion in a roughly opposite position. In addition, the X-ray C-arm device 5 is configured to acquire intraoperative X-ray image data from multiple directions by rotating the X-ray C-ram to an arbitrary angle, and output the acquired intraoperative X-ray image data to the image processing device 7.

The X-ray C-arm of the X-ray C-arm device 5 is provided with a magnetic sensor (not shown in the figure) that detects the magnetic field originated from the position detection device 4 and generates the electric signals according to the detected magnetic field. Then, the electric signals generated in the magnetic sensor are outputted through the cable 15 to the position detection device 4.

In the server 6, for example, pieces of preoperative multi-slice image data 16a-16n acquired by picking up the image of the subject by CT or MRI or the like are stored. The pieces of preoperative multi-slice image data 16a-16n are outputted to the image processing device 7 through a network line of a local area network or the like, for example.

Note that, in the present embodiment, without being limited to the configuration that the pieces of preoperative multi-slice image data 16a-16n are outputted from the server 6 to the image processing device 7, for example, the pieces of preoperative multi-slice image data 16a-16n stored beforehand in a portable storage medium such as a CD-ROM may be read by the image processing device 7.

The display device 8 is provided with a liquid crystal display or the like, for example, and is configured to display the image outputted from the image processing device 7.

The input device 9 is provided with a touch panel or a keyboard or the like, for example, and is configured to be able to input information according to an operation of a user such as an operator to the image processing device 7. Note that, according to the present embodiment, for example, in a scope switch (not shown in the figure) of the operation portion 12 of the endoscope 2 or the like, the information similar to the input device 9 may be inputted.

Figure 2:
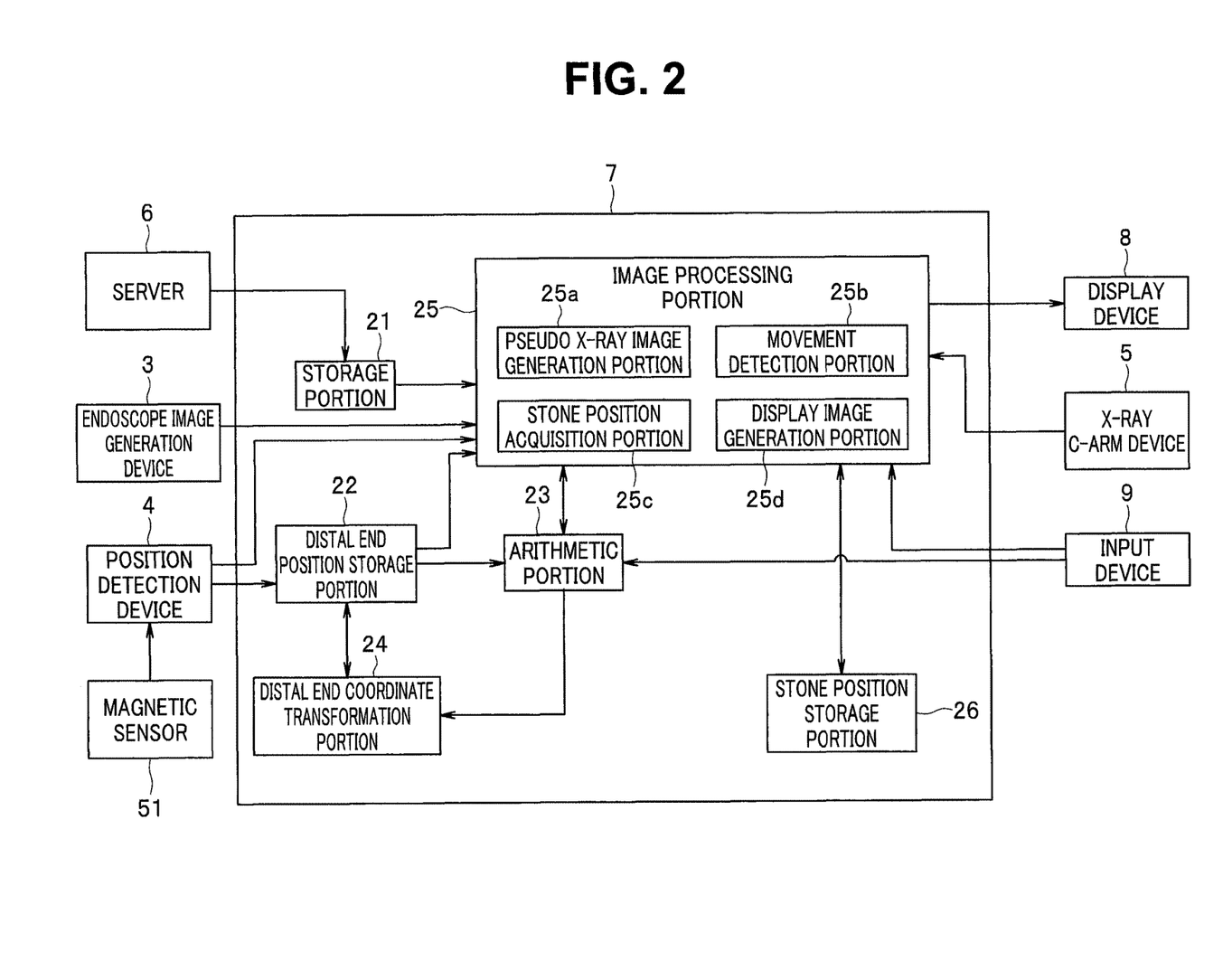
FIG. 2 is a diagram for describing one example of a configuration of an image processing device relating to the embodiment.

Next, a detailed configuration or the like of the image processing device 7 will be described.

As illustrated in FIG. 2, the image processing device 7 is configured including a storage portion 21, a distal end position storage portion 22, an arithmetic portion 23, a distal end coordinate transformation portion 24, an image processing portion 25, and a stone position storage portion 26. FIG. 2 is a diagram for describing one example of the configuration of the image processing device relating to the embodiment.

The storage portion 21 is provided with a storage device such as a hard disk drive, and is configured to store the preoperative multi-slice image data 16a-16n outputted from the server 6.

The distal end position storage portion 22 is configured to store the insertion shape data outputted from the position detection device 4.

Figure 3:
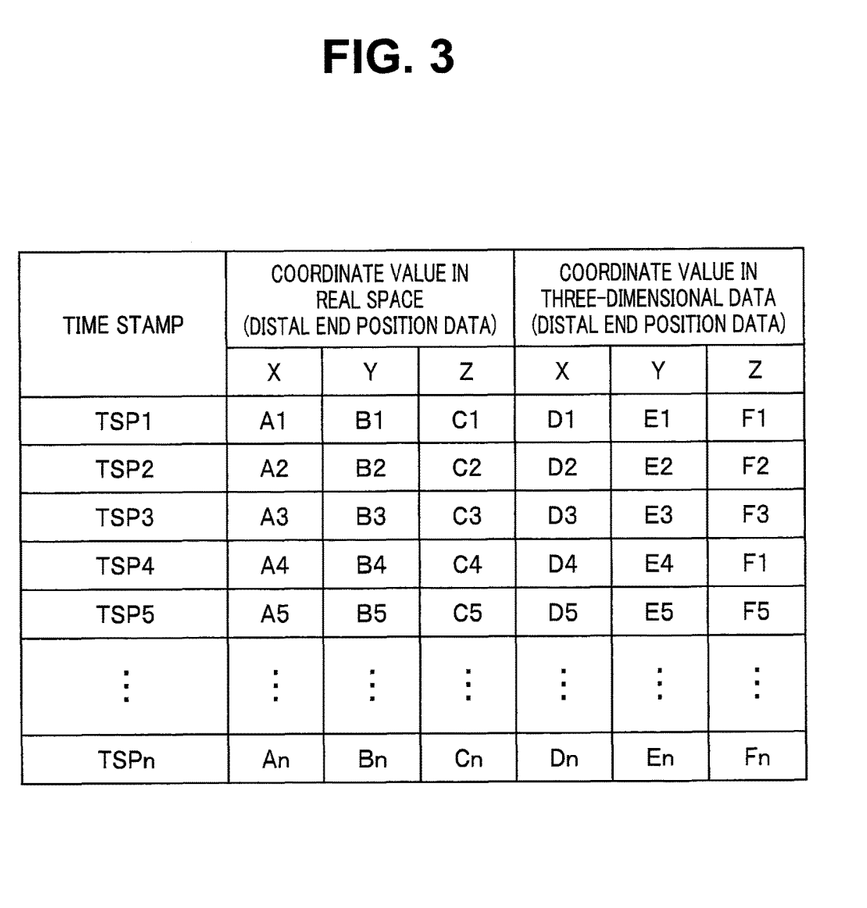
FIG. 3 is a diagram illustrating one example of distal end position data stored in a distal end position storage portion.

The distal end position storage portion 22 is configured to impart a time stamp TSP to the distal end position data and the distal end direction data outputted from the position detection device 4 and store the data. Then, according to such a configuration of the distal end position storage portion 22, for example, as illustrated in FIG. 3, storage is performed in a state that a time stamp TSP1 is imparted to an X coordinate value A1, a Y coordinate value B1 and a Z coordinate value C1 of the distal end position data outputted from the position detection device 4. Note that, for simplification, the distal end direction data is omitted and FIG. 3 is illustrated. FIG. 3 is a diagram illustrating one example of the distal end position data stored in the distal end position storage portion.

The arithmetic portion 23 is configured to calculate a transformation equation for transforming a coordinate value indicating a position in real space to a coordinate value indicating a position in three-dimensional data by comparing a coordinate value of the distal end position data stored in the distal end position storage portion 22 with a coordinate value (described later) of core line data outputted from the image processing portion 25, when it is detected that input of information for executing positioning is performed in the input device 9.

The distal end coordinate transformation portion 24 is configured to transform the distal end position data and the distal end direction data stored in the distal end position storage portion 22 to the coordinate value indicating the position in the three-dimensional data, based on the transformation equation calculated in the arithmetic portion 23. In addition, the distal end coordinate transformation portion 24 is configured to store the distal end position data and the distal end direction data after transformation, the distal end position data and direction data before the transformation, and the time stamp TSP together in the distal end position storage portion 22. Then, according to such processing of the distal end coordinate transformation portion 24, for example, as illustrated in FIG. 3, the X coordinate value A1, the Y coordinate value B1 and the Z coordinate value C1 in real space that are the distal end position data before the transformation, an X coordinate value D1, a Y coordinate value E1 and a Z coordinate value F1 in the three-dimensional data that are the distal end position data after the transformation, and the time stamp TSP1 are stored together in the distal end position storage portion 22. In addition, according to the processing of the distal end coordinate transformation portion 24 as described above, the distal end position data in the three-dimensional data is time-sequentially stored in the distal end position storage portion 22.

That is, according to the processing of the arithmetic portion 23 and the distal end coordinate transformation portion 24 as described above, a coordinate position in three-dimensional model data of a predetermined luminal organ and a coordinate position of a distal end of the insertion portion 11 acquired in the position detection device 4 can be matched.

Figure 4:
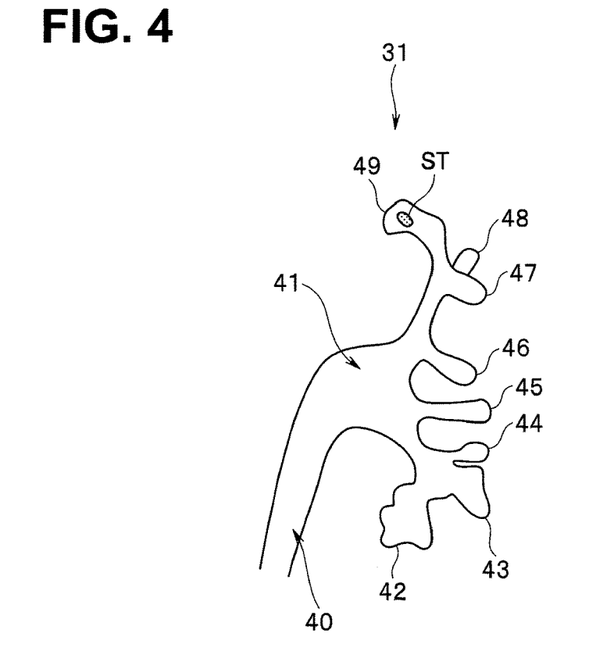
FIG. 4 is a schematic diagram for describing one example of three-dimensional model data of a predetermined luminal organ.
Figure 5:
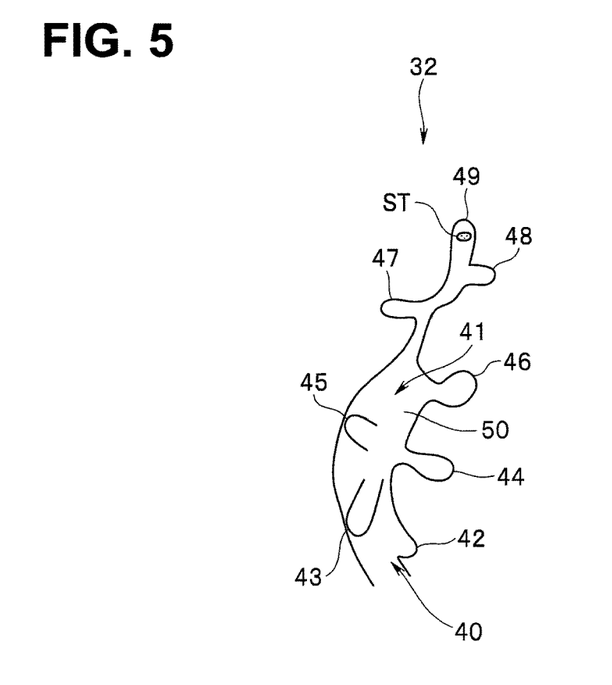
FIG. 5 is a schematic diagram for describing an example different from FIG. 4, of the three-dimensional model data of the predetermined luminal organ.

The image processing portion 25 is configured to generate the three-dimensional model data of the subject using the preoperative multi-slice image data 16a-16n stored in the storage portion 21, and extract three-dimensional model data 31 (see FIG. 4) of the predetermined luminal organ including a ureter 40, a kidney pelvis 41, calyces 42-49, and a stone ST. In addition, the image processing portion 25 is configured to extract the coordinate value of the core line data of a lumen in the three-dimensional model data 31, and output the extracted coordinate value of the core line data to the arithmetic portion 23. In addition, the image processing portion 25 is configured to generate three-dimensional model data 32 (see FIG. 5) for which the three-dimensional model data 31 extracted as described above is rotated by an arbitrary angle in order to observe the predetermined luminal organ from two directions. FIG. 4 is a schematic diagram for describing one example of the three-dimensional model data of the predetermined luminal organ. FIG. 5 is a schematic diagram for describing an example different from FIG. 4, of the three-dimensional model data of the predetermined luminal organ.

Note that the image processing portion 25 of the present embodiment may extract the three-dimensional model data including not only the ureter 40, the kidney pelvis 41 and the calyces 42-49 but also a bladder and a urethra for example, from the three-dimensional model data of the subject. In addition, the image processing portion 25 of the present embodiment is not limited to the portion that extracts the three-dimensional model data of the predetermined luminal organ from the three-dimensional model data of the subject, and may be the portion that reads the three-dimensional model data of the predetermined luminal organ stored beforehand in the server 6 or the storage portion 21, for example.

On the other hand, the image processing portion 25 is configured including a pseudo X-ray image generation portion 25a, a movement detection portion 25b, a stone position acquisition portion 25c, and a display image generation portion 25d.

The pseudo X-ray image generation portion 25a is configured to generate pseudo X-ray image data based on the preoperative multi-slice image data 16a-16n stored in the storage portion 21.

The movement detection portion 25b is configured to calculate a difference value by executing matching processing to the endoscope image data at an initial position of the stone ST and the endoscope image data at a present position of the stone ST, and acquire the calculated difference value as a movement amount of the stone ST. Or, the movement detection portion 25b is configured to calculate a difference value by executing matching processing to the pseudo X-ray image data including the stone ST generated by the pseudo X-ray image generation portion 25a and the X-ray image data obtained by picking up the image of the stone ST existing inside the subject by the X-ray C-arm device 5, and acquire the calculated difference value as a movement amount of the stone ST.

Note that the endoscope image data at the initial position of the stone ST is assumed to be outputted from the endoscope image generation device 3 as moving image data or still image data obtained by picking up the image of the stone ST before treatment to the stone ST existing inside the subject is performed for example, and stored in a memory or the like not shown in the figure of the image processing portion 25. In addition, the endoscope image data at the present position of the stone ST is assumed to be outputted from the endoscope image generation device 3 as the moving image data or the still image data obtained by picking up the image of the stone ST in the middle of the treatment performed to the stone ST existing inside the subject for example, and stored in the memory or the like not shown in the figure of the image processing portion 25.

The movement detection portion 25b is configured to detect whether or not the stone ST has moved, based on a comparison result for which the movement amount of the stone ST acquired as described above and a predetermined threshold TH are compared or based on a judgement result for which whether or not the information is inputted according to the operation of a switch SW1 (not shown in the figure) of the input device 9 is determined. Note that the switch SW1 is configured, for example, as a switch capable of inputting, to the image processing portion 25, the information for notifying that the stone ST has moved in the case that it is clear that the stone ST is moved according to an intention of a user such as the case that the stone ST is moved to a position suitable for the treatment.

The stone position acquisition portion 25c is configured to acquire the coordinate value indicating the initial position of the stone ST in the three-dimensional model data of the subject, based on the three-dimensional model data of the subject generated using the preoperative multi-slice image data 16a-16n.

The stone position acquisition portion 25c is configured to acquire the coordinate value indicating the present position of the stone ST in the three-dimensional data by projecting the movement amount acquired by the movement detection portion 25b on the pseudo X-ray image data generated by the pseudo X-ray image generation portion 25a based on the transformation equation calculated by the arithmetic portion 23 and the X-ray image pickup position data outputted from the position detection device 4 when the movement of the stone ST is detected by the movement detection portion 25b.

Or, the stone position acquisition portion 25c is configured to read an X coordinate value Dn, a Y coordinate value En and a Z coordinate value Fn (see FIG. 3) of the latest distal end position data to which a time stamp TSPn is imparted from the distal end position storage portion 22, when the movement of the stone ST is detected by the movement detection portion 25b, and acquire the read X coordinate value Dn, Y coordinate value En and Z coordinate value Fn as the coordinate value indicating the present position of the stone ST in the three-dimensional data.

The stone position acquisition portion 25c is configured to successively output the coordinate value indicating the initial position of the stone ST in the three-dimensional data and the coordinate value indicating the present position of the stone ST in the three-dimensional data to the stone position storage portion 26 as stone position data.

The display image generation portion 25d is configured to generate one or more markers M indicating the position of the stone ST in the three-dimensional data based on the stone position data stored in the stone position storage portion 26, and combine the generated markers M with the three-dimensional model data 31 and 32.

Figure 6:
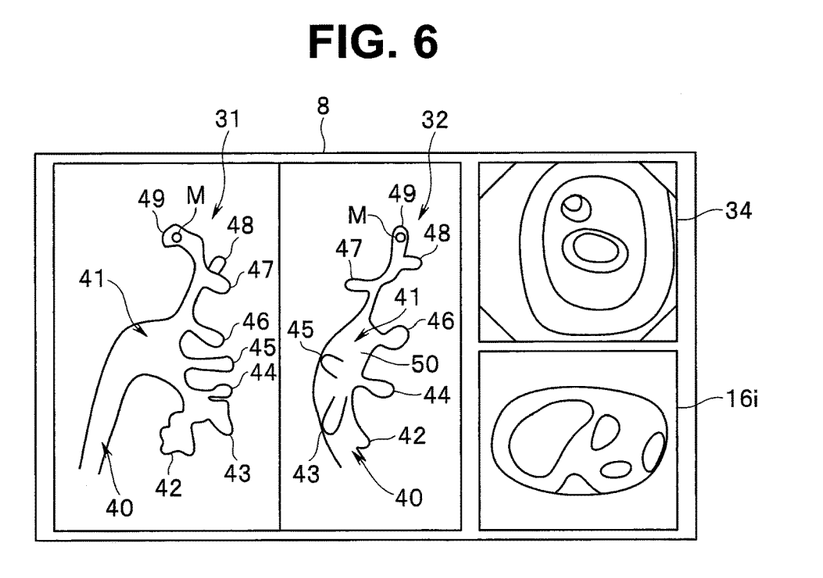
FIG. 6 is a diagram for describing one example of an image displayed at a display device.

The display image generation portion 25d is configured to generate a display image by combining the three-dimensional model data 31 and 32 including the markers M, the endoscope image 34 generated by executing predetermined image processing to the endoscope image data outputted from the endoscope image generation device 3, and one piece of preoperative multi-slice image data 16i selected by the user from the preoperative multi-slice image data 16a-16n stored in the storage portion 21, and output the generated display image to the display device 8. Then, by such processing of the display image generation portion 25d, for example, the image as illustrated in FIG. 6 is displayed at the display device 8. FIG. 6 is a diagram for describing one example of the image displayed at the display device.

The display image generation portion 25d is configured to change a display aspect of a marker indicating the position of the stone ST in the three-dimensional data, based on the stone position data stored in the stone position storage portion 26 when it is detected that the information is inputted according to the operation of a switch SW2 (not shown in the figure) of the input device 9. Note that the switch SW2 is configured as a switch capable of inputting information for selecting one or more markers displayed in the three-dimensional model data 31 and 32 and inputting information for changing the display aspect of the selected one or more markers to a desired display aspect to the image processing portion 25, for example.

Figure 7:
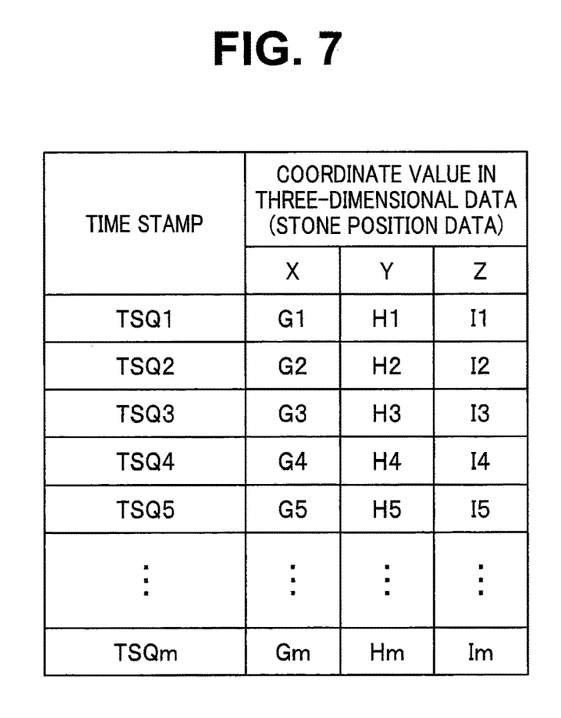
FIG. 7 is a diagram illustrating one example of stone position data stored in a stone position storage portion.

The stone position storage portion 26 is configured to impart a time stamp TSQ to the stone position data successively outputted from the image processing portion 25 and store the data. Then, according to such a configuration of the stone position storage portion 26, for example, as illustrated in FIG. 7, the storage is performed in the state that a time stamp TSQ1 is imparted to an X coordinate value G1, a Y coordinate value H1 and a Z coordinate value I1 indicating the initial position of the stone ST. In addition, according to the configuration of the stone position storage portion 26 as described above, for example, as illustrated in FIG. 7, the storage is performed in the state that a time stamp TSQm is imparted to an X coordinate value Gm, a Y coordinate value Hm and a Z coordinate value Im indicating latest position of the stone ST. That is, according to the configuration of the stone position storage portion 26 as described above, the stone position data successively outputted from the image processing portion 25 is time-sequentially stored. FIG. 7 is a diagram illustrating one example of the stone position data stored in the stone position storage portion.

Figure 8:
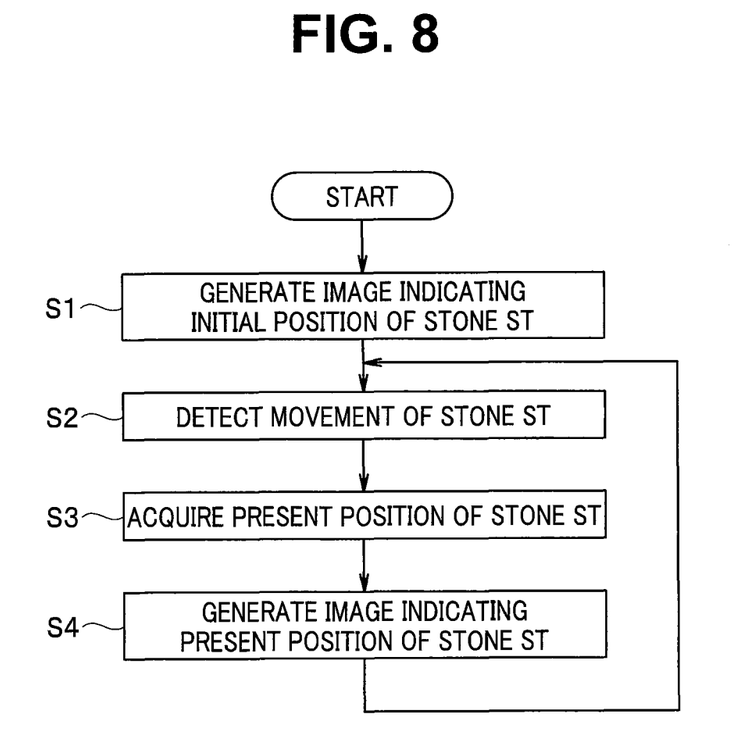
FIG. 8 is a flowchart for describing one example of processing performed in a medical observation system relating to the embodiment.

Subsequently, an action of the present embodiment will be described. FIG. 8 is a flowchart for describing one example of processing performed in the medical observation system relating to the embodiment.

The image processing portion 25 generates the three-dimensional model data of the subject using the preoperative multi-slice image data 16a-16n stored in the storage portion 21, and extracts the three-dimensional model data 31 of the predetermined luminal organ including the ureter 40, the kidney pelvis 41, the calyces 42-49 and the stone ST from the generated three-dimensional model data of the subject.

In addition, the image processing portion 25 generates the three-dimensional model data 32 for which the three-dimensional model data 31 extracted as described above is rotated by the arbitrary angle.

The stone position acquisition portion 25c acquires the coordinate value indicating the initial position of the stone ST in the three-dimensional model data of the subject, based on the three-dimensional model data of the subject generated using the preoperative multi-slice image data 16a-16n, and outputs the acquired coordinate value to the stone position storage portion 26 as the stone position data.

The display image generation portion 25d performs processing as described below as the processing for generating the image indicating the initial position of the stone (step S1 in FIG. 8).

The display image generation portion 25d generates a marker M1 indicating the initial position of the stone ST in the three-dimensional data based on the stone position data stored in the stone position storage portion 26, and combines the generated marker M1 with the three-dimensional model data 31 and 32. In addition, the display image generation portion 25d generates the display image by combining the three-dimensional model data 31 and 32 including the marker M1, the endoscope image 34 and the preoperative multi-slice image data 16i, and outputs the generated display image to the display device 8.

Figure 9:
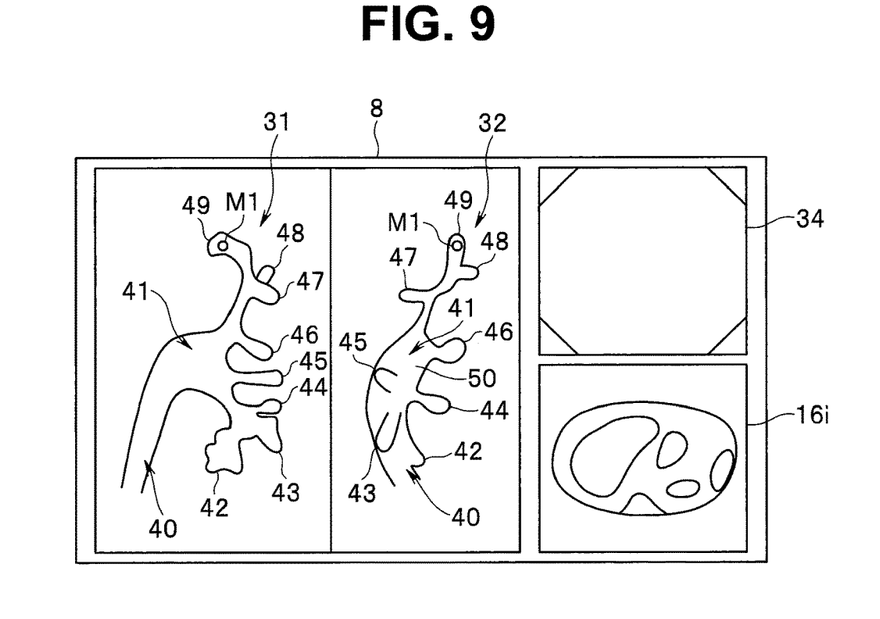
FIG. 9 is a diagram for describing another example of the image displayed at the display device.

Then, by the processing as described above being performed in the display image generation portion 25d, for example, the image as illustrated in FIG. 9 is displayed at the display device 8. FIG. 9 is a diagram for describing another example of the image displayed at the display device. Note that, in FIG. 9, details of the endoscope image 34 displayed at the display device 8 before the insertion portion 11 is inserted to an inside of the subject are omitted for the simplification.

Figure 10:
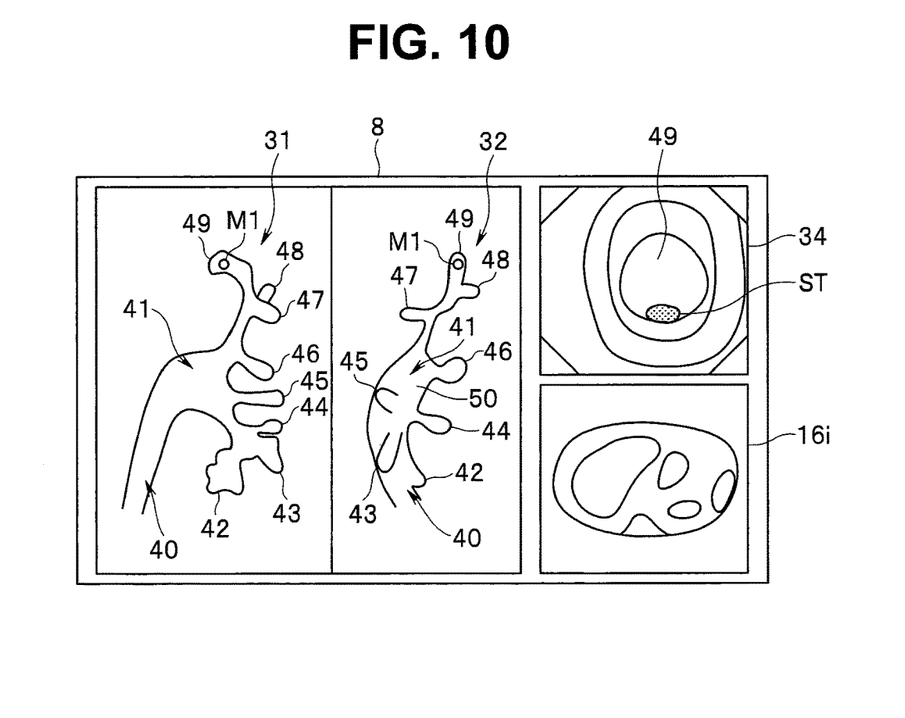
FIG. 10 is a diagram for describing another example of the image displayed at the display device.

The user inserts the insertion portion 11 to the inside of the subject while confirming the position of the marker M1 in the image displayed at the display device 8 and thus arranges the distal end portion 11A of the insertion portion 11 near the stone ST of the calyx 49. Then, according to such an insertion operation by the user, for example, as illustrated in FIG. 10, the endoscope image 34 including the stone ST positioned inside the calyx 49 is displayed at the display device 8. FIG. 10 is a diagram for describing another example of the image displayed at the display device.

Thereafter, the user starts the treatment to the stone ST positioned inside the calyx 49 while confirming the endoscope image 34 displayed at the display device 8.

The movement detection portion 25b performs one piece of processing from individual pieces of processing described below as the processing for detecting the movement of the stone ST (step S2 in FIG. 8).

The movement detection portion 25b calculates the difference value by executing the matching processing to the endoscope image data at the initial position of the stone ST and the endoscope image data at the present position of the stone ST, and acquires the calculated difference value as a movement amount DA of the stone ST. Then, the movement detection portion 25b compares the movement amount DA with a predetermined threshold TH1, and detects the movement of the stone ST in the case of obtaining the comparison result that the movement amount DA is equal to or larger than the predetermined threshold TH1.

The movement detection portion 25b calculates the difference value by executing the matching processing to the pseudo X-ray image data including the stone ST generated by the pseudo X-ray image generation portion 25a and the X-ray image data obtained by picking up the image of the stone ST existing inside the subject by the X-ray C-arm device 5, and acquires the calculated difference value as a movement amount DB of the stone ST. Then, the movement detection portion 25*b* compares the movement amount DB with a predetermined threshold TH2, and detects the movement of the stone ST in the case of obtaining the comparison result that the movement amount DB is equal to or larger than the predetermined threshold TH2.

The movement detection portion 25*b* determines whether or not the information is inputted according to the operation of the switch SW1 of the input device 9, and detects that the stone ST has moved in the case of obtaining the judgement result that the information is inputted according to the operation of the switch SW1.

The stone position acquisition portion 25*c* performs one piece of processing from individual pieces of processing described below as the processing for acquiring the present position of the stone ST when the movement of the stone ST is detected by the movement detection portion 25*b* (step S3 in FIG. 8).

The stone position acquisition portion 25*c* acquires the coordinate value indicating the present position of the stone ST in the three-dimensional data by projecting the movement amount DA or DB acquired by the movement detection portion 25*b* on the pseudo X-ray image data generated by the pseudo X-ray image generation portion 25*a*, based on the transformation equation calculated by the arithmetic portion 23 and the X-ray image pickup position data outputted from the position detection device 4, when the movement of the stone ST is detected by the movement detection portion 25*b*. Then, the stone position acquisition portion 25*c* outputs the coordinate value indicating the present position of the stone ST in the three-dimensional data to the stone position storage portion 26 as the stone position data.

The stone position acquisition portion 25*c* reads the X coordinate value Dn, the Y coordinate value En and the Z coordinate value Fn of the latest distal end position data to which the time stamp TSPn is imparted from the distal end position storage portion 22, when the movement of the stone ST is detected by the movement detection portion 25*b*, and acquires the read X coordinate value Dn, Y coordinate value En and Z coordinate value Fn as the coordinate value indicating the present position of the stone ST in the three-dimensional data. Then, the stone position acquisition portion 25*c* outputs the coordinate value indicating the present position of the stone ST in the three-dimensional data to the stone position storage portion 26 as the stone position data.

The display image generation portion 25*d* including a function as a position information presentation portion performs processing as described below as the processing for generating the image indicating the present position of the stone (step S4 in FIG. 8).

The display image generation portion 25*d* generates a marker Mn indicating the present position of the stone ST in the three-dimensional data based on the latest stone position data stored in the stone position storage portion 26, combines the generated marker Mn with the three-dimensional model data 31 and 32, and eliminates the marker generated before the generated marker Mn from the three-dimensional model data 31 and 32. In addition, the display image generation portion 25*d* generates the display image by combining the three-dimensional model data 31 and 32 including the marker Mn, the endoscope image 34, and the preoperative multi-slice image data 16*i*, and outputs the generated display image to the display device 8.

Figure 11:
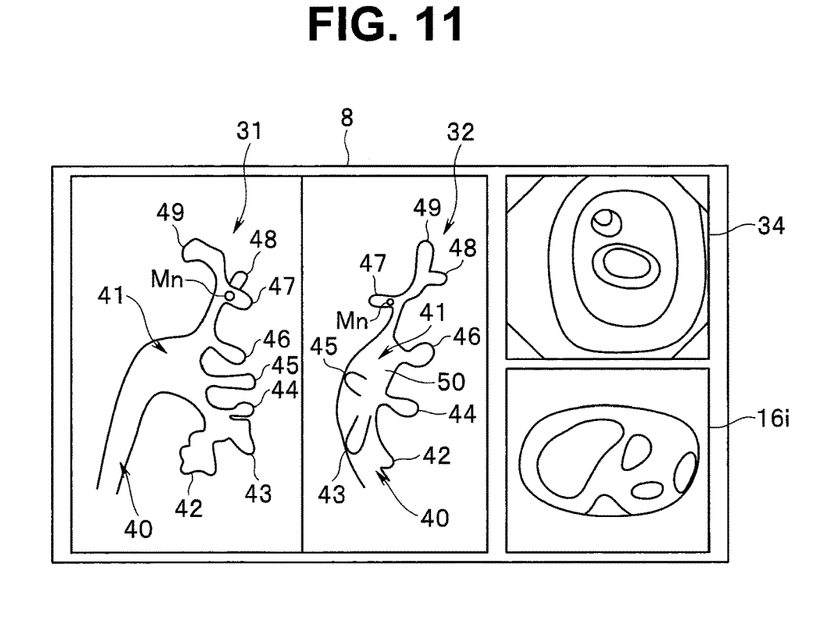
FIG. 11 is a diagram for describing another example of the image displayed at the display device.

Then, by the processing as described above being performed in the display image generation portion 25*d*, for example, the image as illustrated in FIG. 11 is displayed at the display device 8. FIG. 11 is a diagram for describing another example of the image displayed at the display device.

That is, according to the present embodiment, by repeatedly performing the processing of steps S2-S4 in FIG. 8, the marker indicating the present position of the stone ST can be displayed roughly in real time in the three-dimensional model data of the predetermined luminal organ. As a result, according to the present embodiment, burdens of an operator who performs the treatment relating to removal of the stone can be reduced.

Note that the display image generation portion 25*d* of the present embodiment is not limited to the portion that generates the display image by combining the marker indicating the position of the stone ST with the three-dimensional model data 31 of the predetermined luminal organ, and may be the portion that generates the display image by combining the marker with the three-dimensional model data of the subject before the three-dimensional model data 31 of the predetermined luminal organ is extracted, or may be the portion that generates the display image by combining the marker with the pseudo X-ray image data generated by the pseudo X-ray image generation portion 25*a*, for example.

In addition, the display image generation portion 25*d* of the present embodiment is not limited to the portion that performs the processing described above in step S4 in FIG. 8, and may perform processing of coloring the plurality of markers including at least the marker Mn in mutually different colors and combining the plurality of colored markers with the three-dimensional model data 31 and 32 when the input of the information according to the operation of the switch SW2 of the input device 9 is detected, for example.

In addition, the display image generation portion 25*d* of the present embodiment may be the portion that generates the display image which displays the marker indicating the position of the stone ST and a comment imparted to the marker according to the operation of the input device 9 together, for example.

Figure 12:
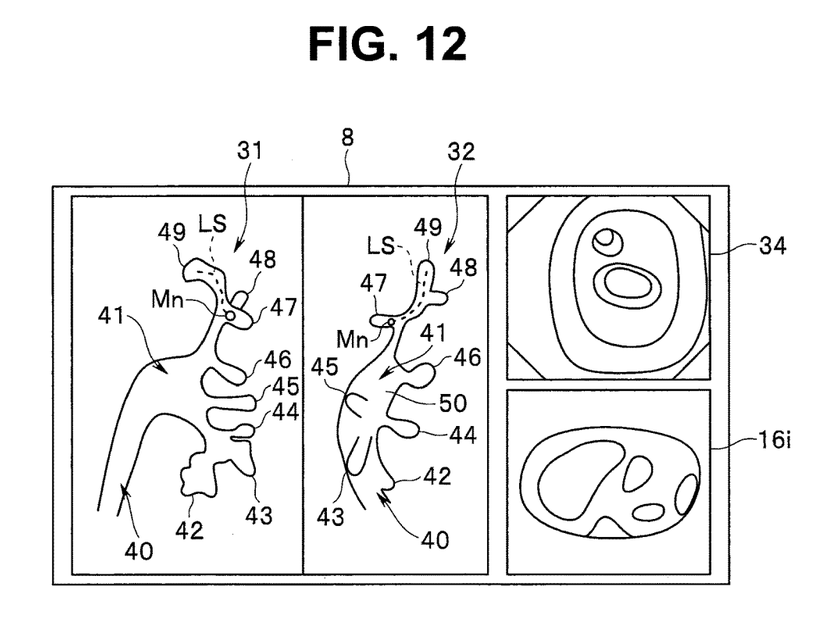
FIG. 12 is a diagram for describing another example of the image displayed at the display device.

In addition, the display image generation portion 25*d* of the present embodiment is not limited to the portion that performs the processing described above in step S4 in FIG. 8, and may generate the marker Mn indicating the present position of the stone ST in the three-dimensional data and a line segment LS indicating a moving track of the stone ST in the three-dimensional data from the marker M1 to the marker Mn respectively and combine the generated marker Mn and the line segment LS with the three-dimensional model data 31 and 32 when the input of the information according to the switch SW2 of the input device 9 is detected, for example. In addition, in such a case, the moving track of the stone ST maybe created by using the stone position data stored in the stone position storage portion 26, or the moving track of the stone ST may be created by using the information stored time-sequentially in the distal end position storage portion 22 (see FIG. 3). Furthermore, in the above-described case, the moving track of the stone ST may be created (inputted) manually according to the operation of the input device 9, or the like, by the user such as the operator. Then, in the case that the processing as described above is performed in the display image generation portion 25*d*, for example, the image as illustrated in FIG. 12 is displayed at the display device 8. FIG. 12 is a diagram for describing another example of the image displayed at the display device.

Note that the present invention is not limited to the embodiment described above, and it is needless to say that various changes and applications are possible without changing a subject matter of the present invention.

What is claimed is:

1. A medical observation system comprising:
   a position information storage portion configured to perform processing for storing first position information which is information indicating an initial position of an object for executing treatment in a three-dimensional image generated based on a plurality of tomographic images of a subject;
   a movement detection portion configured to detect movement of the object for executing the treatment;
   a position information acquisition portion configured to perform processing for acquiring second position information which is information indicating a present position of the object for executing the treatment in the three-dimensional image when the movement of the object for executing the treatment is detected by the movement detection portion; and
   a display image generation portion configured to update a position of the object for executing the treatment in the three-dimensional image from the first position information to the second position information in a case that the second position information is acquired by the position information acquisition portion, and generate an image superimposed on the three-dimensional image or on a pseudo fluoroscopic image generated based on the plurality of tomographic images.

2. The medical observation system according to claim 1, wherein the movement detection portion detects the movement of the object for executing the treatment, based on a picked-up image of the object for executing the treatment existing in the subject.

3. The medical observation system according to claim 1, wherein the position information storage portion time-sequentially stores the second position information acquired by the position information acquisition portion.

4. The medical observation system according to claim 1, wherein the movement detection portion detects the movement of the object for executing the treatment based on an endoscope image of the object for executing the treatment existing inside the subject, the endoscope image being picked up using an endoscope inserted into the subject.

5. The medical observation system according to claim 4, wherein the movement detection portion acquires a movement amount from the initial position of the object for executing the treatment based on the endoscope image, and detects the movement of the object for executing the treatment in a case that the acquired movement amount is equal to or larger than a predetermined threshold.

6. The medical observation system according to claim 5, wherein the movement detection portion acquires the movement amount from the initial position of the object for executing the treatment based on the endoscope image, and the position information acquisition portion acquires the second position information by projecting the movement amount acquired by the movement detection portion on the pseudo fluoroscopic image when the movement of the object for executing the treatment is detected by the movement detection portion.

7. The medical observation system according to claim 5, wherein the position information acquisition portion acquires the second position information by projecting the movement amount acquired by the movement detection portion on the pseudo fluoroscopic image.

8. The medical observation system according to claim 1, wherein the movement detection portion detects the movement of the object for executing the treatment based on the pseudo fluoroscopic image including the object for executing the treatment, and a fluoroscopic image of the object for executing the treatment existing inside the subject, the fluoroscopic image being picked up using radiation transmitted through the subject.

9. The medical observation system according to claim 8, wherein the movement detection portion acquires a movement amount from the initial position of the object for executing the treatment based on the pseudo fluoroscopic image and the fluoroscopic image, and detects the movement of the object for executing the treatment in a case that the acquired movement amount is equal to or larger than a predetermined threshold.

10. The medical observation system according to claim 9, wherein the movement detection portion acquires the movement amount from the initial position of the object for executing the treatment based on the fluoroscopic image, and
    the position information acquisition portion acquires the second position information by projecting the movement amount acquired by the movement detection portion on the pseudo fluoroscopic image when the movement of the object for executing the treatment is detected by the movement detection portion.

11. The medical observation system according to claim 9, wherein the position information acquisition portion acquires the second position information by projecting the movement amount acquired by the movement detection portion on the pseudo fluoroscopic image.

12. The medical observation system according to claim 1, further comprising:
    a position detection portion configured to detect a position in real space of a distal end portion of an endoscope inserted into the subject at every predetermined time interval;
    a position information conversion portion configured to perform processing for converting the position in real space of the distal end portion detected by the position detection portion to distal end position information which is information indicating the position in the three-dimensional image; and
    a distal end position information storage portion configured to time-sequentially store the distal end position information,
    wherein the position information acquisition portion reads latest distal end position information from the distal end position information storage portion and acquires the read latest distal end position information as the second position information when the movement of the object for executing the treatment is detected by the movement detection portion.

* * * * *